(12) United States Patent
Ueyama et al.

(10) Patent No.: US 7,981,405 B2
(45) Date of Patent: Jul. 19, 2011

(54) COSMETIC HAIR PREPARATION

(75) Inventors: Kenichi Ueyama, Tokyo (JP); Michiko Tada, Tokyo (JP)

(73) Assignee: Kao Corporation, Tokyo (JP)

( * ) Notice: Subject to any disclaimer, the term of this patent is extended or adjusted under 35 U.S.C. 154(b) by 1240 days.

(21) Appl. No.: 10/536,276

(22) PCT Filed: Nov. 20, 2003

(86) PCT No.: PCT/JP03/14791
§ 371 (c)(1),
(2), (4) Date: Mar. 1, 2006

(87) PCT Pub. No.: WO2004/047777
PCT Pub. Date: Jun. 10, 2004

(65) Prior Publication Data
US 2006/0165624 A1 Jul. 27, 2006

(30) Foreign Application Priority Data
Nov. 26, 2002 (JP) ................. 2002-342404

(51) Int. Cl.
*A61K 8/02* (2006.01)
*A61K 8/18* (2006.01)
*A61Q 5/00* (2006.01)
*A61Q 5/06* (2006.01)

(52) U.S. Cl. .................. 424/70.11; 424/70.1; 424/400; 424/401

(58) Field of Classification Search .......................... None
See application file for complete search history.

(56) References Cited

U.S. PATENT DOCUMENTS

| | | | | |
|---|---|---|---|---|
| 3,980,769 A | * | 9/1976 | Ghilardi et al. | 510/124 |
| 5,393,452 A | * | 2/1995 | Raleigh et al. | 424/70.121 |
| 5,683,685 A | * | 11/1997 | Hirano et al. | 424/78.03 |
| 6,217,855 B1 | * | 4/2001 | Itou et al. | 424/70.2 |
| 6,569,412 B2 | * | 5/2003 | Yamaguchi et al. | 424/70.1 |
| 2002/0037266 A1 | * | 3/2002 | Terazaki et al. | 424/70.12 |
| 2002/0157682 A1 | * | 10/2002 | Ueyama et al. | 132/221 |

FOREIGN PATENT DOCUMENTS

| | | |
|---|---|---|
| EP | 529437 | 3/1993 |
| EP | 0 858 794 A2 | 8/1998 |
| EP | 0 978 272 A1 | 2/2000 |
| EP | 1 118 319 A1 | 7/2001 |
| EP | 1174112 | 1/2002 |
| GB | 2321595 | 8/1998 |
| JP | 6-172131 | 6/1994 |
| JP | 06-298625 | 10/1994 |
| JP | 07-112921 | 5/1995 |
| JP | 08-198732 | 8/1996 |
| JP | 09-301831 | 11/1997 |
| JP | 10-081614 | 3/1998 |
| JP | 10-218738 | 8/1998 |
| JP | 11-060447 | 3/1999 |
| JP | 2000-109411 | 4/2000 |
| JP | 2001-031531 | 2/2001 |
| JP | 2001-192326 | 7/2001 |
| JP | 2001-220321 | 8/2001 |
| JP | 2002-029938 | 1/2002 |
| JP | 2002-047141 | 2/2002 |
| JP | 2002-047142 | 2/2002 |

* cited by examiner

*Primary Examiner* — Anand Desai
*Assistant Examiner* — Melissa Mercier
(74) *Attorney, Agent, or Firm* — Oblon, Spivak, McClelland, Maier & Neustadt, L.L.P.

(57) ABSTRACT

A leave-on hair cosmetic composition contains (a) malic acid or its salt, (b) lactic acid or its, and (c) an organic solvent selected from the group consisting of aromatic alcohols, N-alkylpyrrolidones, alkylene carbonates, polypropylene glycol, lactones and cyclic ketones.

This hair cosmetic composition is excellent in the effect of substantially modifying the hair property to improve its sleekness, styling ease and touch feel.

25 Claims, No Drawings

COSMETIC HAIR PREPARATION

FIELD OF THE INVENTION

This invention relates to leave-on hair cosmetic compositions, which can improve the sleekness, styling ease and touch feel of the hair.

BACKGROUND OF THE INVENTION

In recent years, it has been reported that under the influence of a chemical treatment with a hair color or a physical treatment by blowing or the like a loss of cuticles from hair surfaces, pores inside the hair due to an outflow of internal hair lipids, or a similar problem takes place and results in dry and loose hair, poor finger-through, low styling ease, a loss of sleekness, or the like.

Leave-on hair cosmetic compositions widely used at present include emulsion-type products containing a wax, higher alcohol, surfactant and the like and gels containing a film-forming polymer (hair-setting polymer) such that they impart styling ease to the hair and prevent dryness and looseness. These hair cosmetic compositions, however, are unable to substantially improve the sleekness and styling ease of the hair, although they can deposit an oil, fat or polymer on the hair surfaces and can temporarily resolve problems such as low styling ease, dryness and looseness.

Some hair cosmetic compositions are intended to modify the hair property. As those developed in attempting to achieve modifications by acting inside the hair, hair cosmetic compositions making use of a specific organic acid and organic solvent are known (see, for example, JP-A-1995-112921,JP-A-1994-172131,JP-A-1997-301831,and JP-A-1994-298625). They provide stiff and hardly manageable hair with suppleness and softness to facilitate hair styling.

DISCLOSURE OF THE INVENTION

The present invention provides a leave-on hair cosmetic composition containing the following ingredients (a) to (c):
(a) malic acid or a salt thereof;
(b) lactic acid or a salt thereof; and
(c) an organic solvent selected from the group consisting of aromatic alcohols, N-alkylpyrrolidones, alkylene carbonates, polypropylene glycol, lactones and cyclic ketones.

MODES FOR CARRYING OUT THE INVENTION

The present invention relates to a leave-on hair cosmetic composition, which substantially modifies the hair property to improve its sleekness and styling ease and to provide it with an excellent touch feel.

The present inventors have found that by the application of a leave-on hair cosmetic composition, which contains (a) malic acid or a salt thereof, (b) lactic acid or a salt thereof and (c) an organic solvent selected from the group consisting of aromatic alcohols, N-alkylpyrrolidones, alkylene carbonates, polypropylene glycol, lactones and cyclic ketones, to hair, the hair is gradually improved in sleekness and is improved especially in the set retention property, styling ease and touch feel at high humidity.

The content of malic acid or a salt thereof as the ingredient (a) (in terms of the amount of malic acid) can be preferably from 0.1 to 30 wt %, more preferably from 0.5 to 20 wt %, even more preferably from 0.5 to 10 wt % in the hair cosmetic composition according to the present invention from the standpoint of making improvements in the sleekness, styling ease and set retention property of hair.

The content of lactic acid or a salt thereof as the ingredient (b) (in terms of the amount of lactic acid) can be preferably from 0.01 to 30 wt %, more preferably from 0.1 to 20 wt %, even more preferably from 0.5 to 10 wt % in the hair cosmetic composition according to the present invention from the standpoint of making improvements in the sleekness, suppleness and softness, and styling ease of hair and preventing dryness and looseness.

As the ingredient (c), an organic solvent selected from the following compounds (c1) to (c5) can be mentioned:
(c1) compounds represented by the following formula (1):

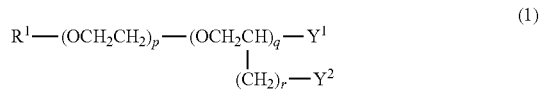

wherein $R^1$ represents a group $R^2$—Ph-$R^3$— ($R^2$: a hydrogen atom, methyl group or methoxy group, $R^3$: a single bond or a saturated or unsaturated, divalent hydrocarbon group having 1 to 3 carbon atoms, Ph: a paraphenylene group), $Y^1$ and $Y^2$ each represent a hydrogen atom or hydroxy group, and p, q and r each denote an integer of from 0 to 5, with a proviso that, when $p=q=0$, $Y^1$ is a hydroxy group and $R^1$ is other than the group $R^2$—Ph-;

(c2) N-alkyl or N-alkenylpyrrolidones wherein an alkyl group or alkenyl group having 1 to 18 carbon atoms is bonded to the nitrogen atom thereof;

(c3) ethylene carbonate or propylene carbonate;

(c4) polypropylene glycol having a number average molecular weight of from 200 to 5,000,preferably from 200 to 1,000;and (c5) lactones or cyclic ketones represented by the following formula (2), (3) or (4):

wherein X represents a methylene group or oxygen atom, $R^4$ and $R^5$ represent different substituent groups, and a and b each denote 0 or 1.

Among organic solvents of the ingredient (c), the compounds (c1) can include benzyl alcohol, cinnamyl alcohol, phenethyl alcohol, p-anisyl alcohol, p-methylbenzyl alcohol, phenoxyethanol, 2-benzyloxyethanol, and the like. The compounds (c2) can include N-methylpyrrolidone, N-octylpyrrolidone, N-laurylpyrrolidone, and the like. In the lactones or cyclic ketones (c5), $R^4$ and $R^5$ in the formulas (2) to (4) can each be preferably a linear, branched or cyclic alkyl group, hydroxy group, sulfonic group, phosphoric group, carboxy group, phenyl group, sulfoalkyl group, phosphoalkyl group, carboxyalkyl group, or the like, and in the case of γ-lactones or δ-lactones, $R^4$ and $R^5$ in the formulas (2) to (4) can each be preferably a linear or branched alkyl group having 1 to 6 carbon atoms, for example, a methyl group, ethyl group, propyl group, isopropyl group, butyl group or the like substituted at the γ-position or δ-position (namely, the methylene adjacent to the hetero oxygen atom), respectively. When increased water solubility is desired for the compounds (2) to (4), it is desired to contain as $R^4$ or $R^5$ an acidic group such as a sulfonic group, phosphoric group or carboxylic group or an alkyl group substituted by one or more of such acidic groups. Among lactones and cyclic lactones as (c5), the lactones can include γ-butyrolactone, γ-caprolactone, γ-valerolactone, δ-valerolactone, δ-caprolactone, δ-heptanolactone, and the like. From the standpoint of the stability of the lactones, however, γ-lactones, such as γ-butyrolactone and γ-caprolactone, are preferred. The cyclic ketones can include cyclopentanone, cyclohexanone, cycloheptanone, 4-methylcycloheptanone, and the like. Preferred ingredients for (c) can include benzyl alcohol, benzyloxyethanol, propylene carbonate, and polypropylene glycol (number average molecular weight: 300 to 500, especially 400).

Further, the ingredient (c) for use in the present invention preferably has an octanol-water partition coefficient (log P) at 25° C. of from −2 to 3, more preferably from −1 to 2 for the promotion of penetration. It is to be noted that log P is an index indicating the partition of substance between an octanol phase and a water phase and is defined by the below-described formula, and some examples of its calculation values are disclosed in Chemical Reviews, 71(6) (1971). It is also to be noted that in the present invention, each log P means a value as measured at 25° C. by the method described in "Measurement Methods of (1-Octanol/Water) Partition Coefficients of Chemical Substances <Part 1>" of the Law Concerning the Examination and Regulation of Manufacture, etc. of Chemical Substances, Revised $4^{th}$ Edition (The Chemical Daily Co., Ltd.).

$$\log P = \log([\text{substance}]_{Octanol}/[\text{substance}]_{water})$$

wherein $[\text{substance}]_{Octanol}$ indicates the molar concentration of the substance in a 1-octanol phase, and $[\text{substance}]_{water}$ indicates the molar concentration of the substance in a water phase.

Specific log Ps of the primary ingredients (c) are: benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41), and γ-butyrolactone (−0.64).

Preferably, the ingredient (c) is liquid at 25° C., and two or more kinds can be used in combination. From the standpoint of the feel during application, the sleekness of hair and promotions of modifying effects (an improvement in elasticity, an improvement in moisture resistance, etc.), its content can be preferably from 0.1 to 40 wt %, more preferably from 0.5 to 10 wt %, even more preferably from 1 to 5 wt % in the hair cosmetic composition according to the present invention.

Malic acid or a salt thereof as the ingredient (a) involves a problem in the feeling of touch in that the hair becomes hard or stiff, although it is highly effective for the internal modifications of the hair (a repair of cavities, etc.) and also highly effective for the improvements of set retention and styling ease. Lactic acid or a salt thereof as the ingredient (b), on the other hand, is effective for the internal modifications of the hair, although it is inferior to the ingredient (a) in the improving effects of set retention and styling ease. Nonetheless, the ingredient (b) is excellently effective for the improvements of the feeling of touch (smoothness and a moist feel), therefore the combined use of both of the ingredients can simultaneously achieve high hair modifying effects (setting ease and sleekness) and a touch-feel improving effect. The ingredient (a) and ingredient (b) can be used at a weight ratio ranging, in terms of acids, preferably from 10/1 to 1/10, more preferably from 4/1 to 1/4. As their salts, water-soluble salts such as sodium salts can be used as needed.

The hair cosmetic composition according to the present invention can additionally contain ethanol. Ethanol contributes to the solubilization or stable dispersion of the ingredient (c). It also contributes to the solubilization of the ingredients (a) and (b), and as a consequence, their penetration into the hair is promoted. The content of ethanol can be preferably from 0.01 to 50 wt %, more preferably from 1 to 20 wt % in the hair composition according to the present invention. From the standpoint of safety, the content of ethanol can preferably be in such a relationship with the content of the ingredient (c) that the weight ratio of ethanol to the ingredient (c) is from 40/1 to 2/1.

In the hair cosmetic composition according to the present invention, a hair-setting polymer may be additionally included from the viewpoint of hairdressing properties, improvements in the adhesion to the hair and the feeling of touch, an early manifestation of the hair-modifying effects, and the viscosity adjustment and stability of the composition. Examples of such a polymer include polyvinylpyrrolidone-based, high molecular compounds such as polyvinylpyrrolidone, vinylpyrrolidone/vinyl acetate copolymer, vinylpyrrolidone/vinyl acetate/vinyl propionate terpolymer, vinylpyrrolidone/alkyl aminoacrylate (quaternized) copolymers, vinylpyrrolidone/acrylate/(meth)acrylic acid copolymers, and vinylpyrrolidone/alkyl aminoacrylate/vinylcaprolactam copolymers; acidic, vinyl-ether-based, high molecular compounds such as methyl vinyl ether/ alkyl half ester of maleic anhydride copolymer; acidic, polyvinyl-acetate-based, high molecular compounds such as vinyl acetate/crotonic acid copolymer, vinyl acetate/crotonic acid/vinyl neodecanoate copolymer, and vinyl acetate/crotonic acid/vinyl propionate copolymer; acidic, acrylic high molecular compounds such as (meth)acrylic acid/(meth)acrylate ester copolymers and acrylic acid/alkyl acrylate/alkylacrylamide copolymers; amphoteric, acrylic high molecular compounds such as N-methacryloylethyl-N,N-dimethylammonium-α-N-methylcarboxybetaine/butyl methacrylate copolymer, and hydroxypropyl acrylate/butylaminoethyl methacrylate/octylacrylamide copolymer; basic, acrylic high molecular compounds such as acrylamide-acrylate quadripolymers; cellulose derivatives such as cationic cellulose derivatives; and chitin-chitosan derivatives such as hydroxypropyl chitosan, carboxymethyl chitin, and carboxymethyl chitosan. Among these hair-setting polymers, cationic polymers and amphoteric polymers are preferred with cationic polymers being more preferred, from the viewpoint of an improvement in the feeling of touch and an early manifestation of the hair-modifying effects.

These hair-setting polymers may be used either singly or in combination. The content of the hair-setting polymer can be preferably from 0.1 to 10 wt %, more preferably from 0.5 to 5 wt % in the hair cosmetic composition according to the present invention.

In the hair cosmetic composition according to the present invention, a silicone and/or an oil ingredient can be included to bring about further improvements in the conditioning effects. Examples of the silicone include dimethylpolysiloxane, polyether-modified silicones, amino-modified silicones, carboxyl-modified silicones, methylphenylpolysiloxane, fatty-acid-modified silicones, alcohol-modified silicones, aliphatic-alcohol-modified silicones, epoxy-modified silicones, fluorine-modified silicones, cyclic silicones, and alkyl-modified silicones. Among these, dimethylpolysiloxane, polyether-modified silicones and amino-modified silicones are preferred. Dimethylpolysiloxane can impart good lubricity to the hair, polyether-modified silicones can impart smoothness to the hair, and amino-modified silicones can impart a moist feel to the hair. In the present invention, various silicones can be used either singly or in combination depending on the required performance. Usable dimethylpolysiloxane can range, depending upon the required touch feel, from one having a viscosity of 5 mm²/s or so to one having a viscosity of 10,000,000 mm²/s or so which is often provided as an emulsion in many instances, although those having viscosities of from 5,000 to 10,000,000 mm²/s are preferred, with those having viscosities of from 50,000 to 10,000,000 mm²/s being preferred. Polyether-modified silicone is a generic term for polyoxyethylene-methylpolysiloxane copolymers and poly(oxyethylene/oxypropylene)methylpolysiloxane copolymers, and those having various HLBs are known. Illustrative commercial products include "SILICONE KF351A", "SILICONE KF353A", "SILICONE KF6008", "SILICONE KF6016", "SILICONE KF6011" and "SILICONE KF6012" (products of Shin-Etsu Chemical Co., Ltd.); and "SH3771C", "SH3773C" and "3775C" (products of Dow Corning Toray Silicone Co., Ltd.). As the amino-modified silicones, amodimethicone oil and its emulsions are preferred. Illustrative commercial products include "AMODIMETHICONE EMULSION SM8704C" (product of Dow Corning Toray Silicone Co., Ltd.) and "KT-1989" and "XF42-B1989" (products of Toshiba Silicone Co., Ltd.).

From the standpoint of finger-through ease and low tackiness, the content of the silicone can be preferably from 0.05 to 20 wt %, more preferably from 0.1 to 10 wt %, even more preferably from 0.5 to 5 wt % in the hair cosmetic composition according to the present invention.

The oil ingredient is used to improve the feeling of styled hair after drying. Examples of the oil ingredient include hydrocarbons such as squalene, squalane, liquid isoparaffin, light liquid isoparaffin, heavy liquid isoparaffin, α-olefin oligomers, liquid paraffin, and cycloparaffin; glycerides such as castor oil, cacao oil, mink oil, avocado oil, and olive oil; waxes such as beeswax, spermaceti, lanolin, microcrystalline wax, ceresin wax, and carnauba wax; higher alcohols such as cetyl alcohol, oleyl alcohol, stearyl alcohol, isostearyl alcohol, and 2-octyldodecanol; esters such as octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut fatty acid, isostearic acid, and isopalmitic acid; and, isostearyl glyceryl ether and polyoxypropylene butyl ether. Among these, preferred ones are branched hydrocarbons such as squalene, squalane, liquid isoparaffin, light liquid isoparaffin, heavy liquid isoparaffin, and α-olefin oligomers.

From the standpoint of good styling ease and low tackiness, the content of the oil ingredient can be preferably from 0.05 to 20 wt %, more preferably from 0.1 to 10 wt %, even more preferably from 0.5 to 5 wt % in the hair cosmetic composition according to the present invention.

From the standpoint of the stability of the system including the solubilization with the solvent, dispersibility and the like and also improvements in the feeling of touch, a surfactant can be included in the hair cosmetic composition according to the present invention. As the surfactant, any one or more of cationic surfactants, nonionic surfactants, amphoteric surfactants and anionic surfactant are usable.

Preferred examples of the cationic surfactants include quaternary ammonium salts represented by the following formula (5):

(5)

wherein $R^6$ and $R^7$ each independently represents a hydrogen atom, an alkyl group having 1 to 28 carbon atoms or a benzyl group with a proviso that at the same time, they are not hydrogen atoms or benzyl groups or are not lower alkyl groups having 1 to 3 carbon atoms, and $Z^-$ represents an anion. Preferably, one of $R^6$ and $R^7$ can be an alkyl group, especially linear alkyl group having 16 to 24 carbon atoms, more preferably 22 carbon atoms, and the other one can be a lower alkyl group having 1 to 3 carbon atoms, especially a methyl group. Examples of the anion $Z^-$ include halide ions such as chloride ion and bromide ion; and organic anions such as ethyl sulfate ion and methyl carbonate ion, with halide ions, especially a chloride ion being preferred.

Preferred examples of the cationic surfactants include mono-long chain alkyl quaternary ammonium salts, among which cetyl trimethylammonium chloride, stearyl trimethylammonium chloride, arachyl trimethylammonium chloride, and behenyl trimethylamionium chloride are preferred, with stearyl trimethylammonium chloride and behenyl trimethylammonium chloride being more preferred.

Preferred examples of the nonionic surfactants include polyoxyalkylene alkyl ethers, polyoxyalkylene alkenyl ethers, higher fatty acid sucrose ester, polyglyceryl fatty acid esters, higher fatty acid mono- or diethanolamides, polyoxyethylene hydrogenated castor oil, polyoxyethylene sorbitan fatty acid esters, polyoxyethylene sorbitol fatty acid esters, alkyl-saccharide-based surfactants, alkylamine oxides, and alkylamidoamine oxides. Among these, polyoxyalkylene alkyl ethers and polyoxyethylene hydrogenated castor oil are preferred, with polyoxyethylene alkyl ethers being more preferred.

Examples of the amphoteric surfactants include imidazoline-based amphoteric surfactants, carbobetaine-based amphoteric surfactants, amidobetaine-based amphoteric surfactants, sulfobetaine-based amphoteric surfactants, hydroxysulfobetaine-based amphoteric surfactants, and amidosulfobetaine-based amphoteric surfactants.

Examples of the anionic surfactants include alkylbenzenesulfonates, alkyl or alkenyl ether sulfates, alkyl- or alkenylsulfates, olefinsulfonates, alkanesulfonates, saturated or unsaturated fatty acid salts, alkyl or alkenyl ether carboxylates, α-sulfofatty acids, N-acylaminoacid surfactants, phosphate mono- or diester surfactants, and sulfosuccinate ester surfactants. Examples of counter ions for the anionic residual groups in the above-described surfactants include alkali metal ions such as sodium ion and potassium ion; alkaline earth metal ions such as calcium ion and magnesium ion; ammonium ion; and alkanolamines having 1 to 3 alkanol groups each having 2 or 3 carbon atoms (for example, monoethanolamine, diethanolamine, triethanolamine, triisopropanolamine, and the like). Examples of counter ions for the cationic residual groups, include halide ions such as chloride ion, bromide ion and iodide ion, methosulfate ion and saccharinate ion.

These surfactants can be used either singly or in combination. From the standpoint of the stability of the system including the solubilization with the solvent, the emulsification of the oil ingredient, and the like, the content of the surfactant can be preferably from 0.01 to 10 wt %, more preferably from 0.05 to 3 wt % in the hair cosmetic composition according to the present invention.

In the hair cosmetic composition according to the present invention, a polyhydric alcohol can also be included additionally. The polyhydric alcohol contributes to the solubilization and stable dispersion of the ingredient (c), and also, acts synergistically with the ingredient (c) to promote improvements in sleekness and the hair-modifying effects. Examples of the polyhydric alcohol include ethylene glycol, glycerol, sorbitol, propylene glycol, 1,3-butylene glycol, and dipropylene glycol, with glycerol being particularly preferred. These polyhydric alcohols can be used either singly or in combination. The content of the polyhydric alcohol can be preferably from 0.1 to 10 wt %, more preferably from 0.5 to 5 wt % in the hair cosmetic composition according to the present invention.

In addition, the hair cosmetic composition according to the present invention can also contain an organic carboxylic acid other than malic acid (a) or lactic acid (b) and/or an inorganic acid. Examples of the organic carboxylic acid include dicarboxylic acids such as malonic acid, succinic acid, glutaric acid, adipic acid, maleic acid, fumaric acid, and phthalic acid; and hydroxycarboxylic acids such as glycolic acid, hydroxyacrylic acid, oxybutyric acid, glyceric acid, and citric acid. Examples of the inorganic acid include phosphoric acid, sulfuric acid, and nitric acid. They can be included at from 0.001 to 10 wt % based on the hair cosmetic composition according to the present invention.

The hair cosmetic composition according to the present invention can be used without any problem insofar as it falls within a pH range of from 1 to 7. From the standpoint of an improvement in the sleekness of hair and an improvement in the styling ease of hair, however, it is preferred to use the hair cosmetic composition according to the present invention in a low pH range, and the pH (25° C.) of a solution diluted 20-fold in water can be preferably in a range of from 2.5 to 4.5, more preferably in a range of from 3 to 4.2. For the adjustment of the pH, it is possible to use an organic carboxylic acid other than the ingredient (a) or (b), an inorganic acid, or a basic substance such as sodium hydroxide or an organic amine.

In addition to the above-described ingredients, ingredients employed in general hair cosmetic compositions can also be added to the hair cosmetic composition according to the present invention as needed depending upon the object. Examples of such ingredients include viscosity increasing agents, antidandruff agents, vitamins, antimicrobial agents, anti-inflammetories, chelating agents, moisturizers (panthenol and the like), pH adjusters, colorants such as dyes and pigments, plant extracts, pearlants, fragrances, ultraviolet light absorbers, antioxidants, and perfumes, and the balance consists of water.

The penetration of the ingredients (a) to (c) into the hair can be promoted by warming the hair after the application of the hair cosmetic composition according to the present invention to the hair. For warming, a dryer, heater, iron or the like can be used. The temperature can be preferably 60° C. or higher, more preferably 70° C. or higher.

As the form of the hair cosmetic composition according to the present invention, a suitable form can be chosen such as a liquid, gel or paste form. A liquid form making use of water or a lower alcohol, especially water as a solvent is preferred.

The hair cosmetic composition according to the present invention can be used preferably as a hair styling product or a hair conditioner. Illustrative formulations include pump sprays, aerosol sprays, pump foams, aerosol foams, gels, and lotions.

EXAMPLES

Example 1

Evaluation Based on Hair Tresses

Hair cosmetic compositions shown in Tables 2 and 3 were formulated, and were evaluated for "setting ease", "body-improving effect", "styling ease", "touch feel", and "sleekness". The results of the evaluation are shown in Tables 2 and 3.

(Ranking Methods)

Evaluation of "Setting Ease"

1) Tresses for the Evaluation

Using the hair of Japanese females not subjected to any chemical treatment such as permanent wave treatment or hair coloring treatment, tresses having a 10 cm length, 1.5 cm width and 1 g weight were prepared. The tresses were subjected twice to a bleaching treatment ("LAVENUS COLOR APPEAL INAZUMA BLEACH", product of Kao Corporation, was used), and were provided as tresses for the evaluation of setting ease.

2) Treatment of the Tresses

Pre-Shampooing Evaluation (Treated Seven Times)

Each tress for the evaluation was shampooed (with "LAVENUS DESIGNING SHAMPOO", product of Kao Corporation), and after towel-dried, an example product or comparative product (hereinafter called "the treatment composition") (0.1 g) was evenly applied, followed by drying for 10 minutes with warm air of 70° C. That treatment was repeated 6 times in total. After shampooing, towel-drying and an application of the treatment composition around, the tress was wrapped a rod having a 4 cm diameter, and was dried for 10 minutes with warm air of 70° C.

Post-Shampooing Evaluation

By evaluating the hair set retention properties after washing off the treatment composition from the hair surfaces, modifying effects on the interior of the hair were examined. Subsequent to the completion of the above-described pre-shampooing evaluation, each tress was shampooed, towel-dried, wrapped around a rod having a 4 cm diameter without applying the treatment composition, and then dried for 10 minutes with warm air of 70° C.

3) Evaluation Procedure and Standards

The set tress was removed from the rod, and combing by a ring comb was conducted twenty times to the tress to unbraid it. The tress was suspended in a thermohygrostat (25° C., 98% RH) to determine the set retention ability. Described specifically, the length of the suspended tress (the distance from a bundled part to the hair ends) was measured. Supposing that the length of the tress shortly after its suspension was 100% set retention, and the length (10 cm) of the original, curl-free tress was 0% set retention, a relative value (%) of the length of the tress after 30 minutes, namely, the percent set retention was determined in accordance with the following formula:

$$\% \text{ set retention} = \frac{(\text{length of the original tress}) - (\text{length of the tress after 30 minutes})}{(\text{length of the original tress}) - (\text{length of the tress shortly after curling})} \times 100$$

The setting ease was ranked in accordance with the following standards:

A: % set retention ≧90%
B: 90%>% set retention ≧60%
C: 60%>% set retention ≧50%
D: 50%>% set retention Evaluation of "Body Improving Effects", "Styling Ease", "Touch Feel (Smoothness, Moist Feel, Softness, Stiffness, Tackiness)", and "Sleekness"

1) Tresses for the Evaluation

Using the hair of Japanese females not subjected to any chemical treatment such as permanent wave treatment or hair coloring treatment, tresses having a 25 cm length and 6 g weight were prepared. The tresses were subjected twice to a bleaching treatment ("LAVENUS COLOR APPEAL INAZUMA BLEACH", product of Kao Corporation, was used), and were provided as tresses for the evaluation.

2) Treatment of the Tresses

Pre-Shampooing Evaluation

Each tress for the evaluation was shampooed (with "LAVENUS DESIGNING SHAMPOO", product of Kao Corporation), and after towel-dried, the treatment composition (0.6 g) was evenly applied, followed by drying for 10 minutes with warm air of 70° C. while combing the tress by using a ring comb. That treatment was repeated 7 times in total.

Post-Shampooing Evaluation

To examine improving effects on the interior of the hair, each tress which had been gone through the above-described pre-shampooing evaluation was shampooed, towel-dried, and then dried for 10 minutes with warm air of 70° C. while combing the tress by using a ring comb.

3) Evaluation Standards

By five expert panelists, organoleptic evaluations were conducted in accordance with the standards shown in Table 1, and ranking of each product was conducted based on an average of evaluation scores.

TABLE 1

| (Body-improving effect) | | (Styling ease) | |
|---|---|---|---|
| 4: | An improvement in body is felt. | 4: | Styled well. |
| 3: | An improvement in body is felt rather fairly. | 3: | Styled rather fairly. |
| 2: | Cannot say whether or not there is a body-improving effect. | 2: | Cannot say whether styled or not. |
| | | 1: | Styled rather poorly. |
| | | 0: | Styled poorly. |
| 1: | No substantial improvement in body is felt. | (Touch feel: moist feel) | |
| | | 4: | Moist. |
| | | 3: | Rather moist. |
| 0: | No improvement in body is felt. | 2: | Cannot say whether moist or not. |
| (Touch feel: smoothness) | | 1: | Rather non-moist. |
| | | 0: | Non-moist. |
| 4: | Smooth. | (Touch feel: stiffness) | |
| 3: | Rather smooth. | 4: | Not stiff. |
| 2: | Cannot say whether smooth or not. | 3: | Rather non-stiff. |
| 1: | Rather non-smooth. | 2: | Cannot say whether stiff or non-stiff. |
| 0: | Non-smooth. | 1: | Rather stiff. |
| (Touch feel: softness) | | 0: | Stiff. |
| 4: | Soft. | (Sleekness) | |
| 3: | Rather soft. | 4: | A marked improvement in sleekness is observed. |
| 2: | Cannot say whether soft or not. | | |
| 1: | Rather non-soft. | 3: | An improvement in sleekness is observed. |
| 0: | Non-soft. | | |
| (Touch feel: tackiness) | | 2: | Cannot say whether or not an improvement in sleekness is observed. |
| 4: | Non-tacky. | | |
| 3: | Rather non-tacky. | | |
| 2: | Cannot say whether tacky or not. | 1: | No improvement in sleekness is observed. |
| 1: | Rather tacky. | 0: | Sleekness has been lost. |
| 0: | Tacky. | | |

<Determination standards>
A: 4 ≧ average evaluation score ≧ 3
B: 3 > average evaluation score ≧ 2
C: 2 > average evaluation score ≧ 1
D: 1 > average evaluation score ≧ 0

TABLE 2

| | | | Example products | | | | | Comparative products | | |
|---|---|---|---|---|---|---|---|---|---|---|
| | | | 1 | 2 | 3 | 4 | 5 | 1 | 2 | 3 |
| Composition (wt %) | | Malic acid | 2.5 | 1.0 | 4.0 | 4.5 | 0.45 | 2.5 | 5.0 | — |
| | | Lactic acid | 2.5 | 4.0 | 1.0 | 0.45 | 4.5 | 2.5 | — | 5.0 |
| | | 2-Benzyloxyethanol | 2.5 | 2.5 | 2.5 | 2.5 | 2.5 | — | 2.5 | 2.5 |
| | | Stearyl trimethylammonium chloride | 0.25 | 0.25 | 0.25 | 0.25 | 0.25 | 0.25 | 0.25 | 0.25 |
| | | Ethanol | 4.5 | 4.5 | 4.5 | 4.5 | 4.5 | 4.5 | 4.5 | 4.5 |
| | | Water | Balance | Balance | Balance | Balance | Balance | Balance | Balance | Balance |
| | | Sodium hydroxide (pH adjuster)* | q.s. | q.s. | q.s. | q.s. | q.s. | q.s. | q.s. | q.s. |
| Evaluation | Pre-shampooing | Setting ease | A | B | A | A | B | D | A | C |
| | | Body-improving effect | B | B | A | B | B | D | B | C |
| | | Styling ease | A | A | A | B | A | C | C | C |
| | | Smoothness | A | A | B | C | A | D | D | C |
| | | Moist feel | B | B | B | B | B | C | C | C |
| | | Softness | B | A | B | C | B | C | C | A |
| | | Stiffness | A | A | A | B | A | C | D | B |
| | | Tackiness | A | A | A | B | B | B | B | B |
| | | Sleekness | A | A | A | A | A | C | A | B |
| | Post-shampooing | Setting ease | A | B | A | A | B | D | A | D |
| | | Body-improving effect | A | B | A | B | B | D | B | C |
| | | Styling ease | A | A | A | A | B | D | D | D |

*Adjusted to pH 3.7 with a 48 wt % aqueous solution of sodium hydroxide.

TABLE 3

|  |  | Example products | | | |
|---|---|---|---|---|---|
|  |  | 6 | 7 | 8 | 9 |
| Composition (wt %) | Malic acid | 2.5 | 2.5 | 2.5 | 2.5 |
|  | Lactic acid | 2.5 | 2.5 | 2.5 | 2.5 |
|  | Benzyl alcohol | 2.5 | — | — | — |
|  | N-methylpyrrolidone | — | 2.5 | — | — |
|  | Propylene carbonate | — | — | 2.5 | — |
|  | Propylene glycol | — | — | — | 2.5 |
|  | Stearyl trimethylammonium chloride | 0.25 | 0.25 | 0.25 | 0.25 |
|  | Ethanol | 4.5 | 4.5 | 4.5 | 4.5 |
|  | Water | Balance | Balance | Balance | Balance |
|  | Sodium hydroxide (pH adjuster)* | q.s. | q.s. | q.s. | q.s. |
| Evaluation | Pre-shampooing Setting ease | A | A | A | B |
|  | Body-improving effect | B | C | C | C |
|  | Styling ease | A | A | A | B |
|  | Smoothness | A | A | B | B |
|  | Moist feel | B | B | A | B |
|  | Softness | B | B | B | C |
|  | Stiffness | A | A | A | B |
|  | Tackiness | A | A | A | B |
|  | Sleekness | A | A | A | A |
|  | Post-shampooing Setting ease | A | B | A | B |
|  | Body-improving effect | B | B | C | C |
|  | Styling ease | A | A | A | B |

*Adjusted to pH 3.7 with a 48 wt % aqueous solution of sodium hydroxide.

From the above results, it has been confirmed that unlike the conventional techniques the present invention can achieve good setting ease, a body-improving effect, styling ease and a touch-feel-improving effect without developing stiffness or tackiness. In addition to the maintenance of the effects even after the removal of surface-deposited ingredients by shampooing, hair-modifying effects have also been ascertained as demonstrated inter alia by the elimination of pores inside the hair.

Example 2

Effects (1) Obtained from the Combined Use with a Hair Setting Polymer

With respect to the hair cosmetic compositions shown in Table 4, evaluation was performed in setting ease in accordance with similar evaluation procedure and evaluation standards as in Example 1 after providing similar tresses for evaluation as those employed for the evaluation of setting ease in Example 1 and applying the below-described treatment. The results of the evaluation are shown in Table 4.

Treatment of Tresses

Provided were two kinds of tresses, one being (warm-air-dried) tresses subjected to the same treatment as the pre-shampooing evaluation in setting ease (treated seven times) in Example 1, and the other being (room-temperature-dried) tresses treated in a similar manner as in the above treatment except that only as the drying in the final stage, the tresses were air-dried by blowing air of room temperature (25° C.) against them for 30 minutes.

TABLE 4

|  |  | Example products | | Comp. product |
|---|---|---|---|---|
|  |  | 1 | 10 | 4 |
| Composition (wt %) | Malic acid | 2.5 | 4.0 | — |
|  | Lactic acid | 2.5 | 1.0 | — |
|  | 2-Benzyloxyethanol | 2.5 | 1.0 | — |
|  | Stearyl trimethyl ammonium chloride | 0.25 | — | — |

TABLE 4-continued

|  |  | Example products | | Comp. product |
|---|---|---|---|---|
|  |  | 1 | 10 | 4 |
|  | Hair setting polymer* | — | 3.0 | 3.0 |
|  | Polyethylene glycol 600 | — | 1.0 | 1.0 |
|  | Polyoxyethylene hydrogenated castor oil (60 E.O.) | — | 0.5 | 0.5 |
|  | Ethanol | 4.5 | 15.0 | 15.0 |
|  | Water | Balance | Balance | Balance |
|  | Sodium hydroxide (pH adjuster)** | q.s. | q.s. | q.s. |
| Setting ease | Dried at room temperature | B | A | C |
|  | Dried with warm air | A | A | C |

*N-methacryloyloxyethyl-N,N-dimethylammonium-α-N-methylcarboxybetaine-alkyl methacrylate copolymer solution (30% ethanol solution).
**Adjusted to pH 3.7 with a 48 wt % aqueous solution of sodium hydroxide.

From the above-described results, it has been confirmed that by the addition of the hair setting polymer, the setting ease upon drying at room temperature is improved. Further, the comparative product 4 had significantly-reduced setting ease because surface coatings were damaged when the tress was unbraided with a comb, while the example products had good setting performance because they had modifying effects on the hair itself.

Example 3

Effects (2) Obtained from the Combined Use with a Hair Setting Polymer

With respect to the hair cosmetic compositions shown in Table 5, evaluation was performed in setting ease in accordance with similar evaluation procedure and evaluation standards as in Example 1 after providing similar tresses for evaluation as those employed for the evaluation of setting ease in Example 1 and applying the below-described treatment. The results of the evaluation are shown in Table 5.

Pre-Shampooing Evaluation (Treated Once)

Each tress for the evaluation was shampooed (with "LAVENUS DESIGNING SHAMPOO", product of Kao Corporation), and after towel-dried, the treatment composition (0.1 g) was evenly applied. The tress was wrapped on a rod having a 4 cm diameter, and was then dried for 10 minutes with warm air of 70° C.

Pre-Shampooing Evaluation (Treated Three Times)

Each tress for the evaluation was shampooed, and after towel-dried, the treatment composition (0.1 g) was evenly applied, followed by drying for 10 minutes with warm air of 70° C. That treatment was repeated twice in total. After shampooing and then applying the treatment composition in a similar manner as described above, the tress was wrapped around a rod having a 4 cm diameter and was dried for 10 minutes with warm air of 70° C.

Pre-Shampooing Evaluation (Treated Seven Times)

A similar treatment as the "Pre-shampooing evaluation (treated seven times)" in Example 1 was conducted.

Post-Shampooing Evaluation

Subsequent to the completion of the three kinds of pre-shampooing evaluations, each tress was shampooed, towel-dried, wrapped around a rod having a 4 cm diameter without applying the treatment composition, and then dried for 10 minutes with warm air of 70° C.

TABLE 5

|  |  | Example products | | | | |
| --- | --- | --- | --- | --- | --- | --- |
|  |  | 1 | 11 | 12 | 13 | 14 |
| Composition (wt %) | Malic acid | 2.5 | 2.5 | 2.5 | 2.5 | 2.5 |
|  | Lactic acid | 2.5 | 2.5 | 2.5 | 2.5 | 2.5 |
|  | 2-Benzyloxyethanol | 2.5 | 2.5 | 2.5 | 2.5 | 2.5 |
|  | Stearyl trimethylammonium chloride | 0.25 | 0.25 | 0.25 | 0.25 | 0.25 |
|  | Polyquartanium-11 | — | 0.30 | — | — | — |
|  | Polyquartanium-46 | — | — | 0.30 | — | — |
|  | Polyquartanium-55 | — | — | — | 0.30 | — |
|  | Hair setting polymer* | — | — | — | — | 1.00 |
|  | Ethanol | 4.5 | 4.5 | 4.5 | 4.5 | 4.5 |
|  | Water | Balance | Balance | Balance | Balance | Balance |
|  | Sodium hydroxide (pH adjuster)** | q.s. | q.s. | q.s. | q.s. | q.s. |
| Setting ease | Treated once — Pre-shampooing | D | B | B | B | B |
|  | Post-shampooing | D | C | C | C | C |
|  | Treated three times — Pre-shampooing | B | A | A | A | A |
|  | Post-shampooing | C | B | B | B | B |
|  | Treated seven times — Pre-shampooing | A | A | A | A | A |
|  | Post-shampooing | A | A | A | A | A |

*N-methacryloyloxyethyl-N,N-dimethylammonium-α-N-methylcarboxybetaine-alkyl methacrylate copolymer solution (30 wt % ethanol solution).
**Adjusted to pH 3.7 with a 48 wt % aqueous solution of sodium hydroxide.

From the above-described results, it has been ascertained that the addition of the hair-setting polymer makes improvements in pre-shampooing and post-shampooing setting ease at fewer treatment times. This also suggests that the improving effects on the hair itself can be promoted by the addition of the polymer.

Example 4

Evaluation in Actual Use

Example Product 15

|  | (wt %) |
| --- | --- |
| Malic acid | 2.5 |
| Lactic acid | 2.5 |
| Stearyl trimethylammonium chloride | 0.25 |
| Polyoxyethylene hydrogenated castor oil (60 E.O.) | 0.2 |
| Trimethylglycine | 0.2 |
| 2-Benzyloxyethanol | 2.5 |
| Ethanol | 10.0 |
| Fragrance | 0.05 |
| Water | Balance |

The hair cosmetic composition of the example product 15 was placed in pump mist bottles and was then used by the following panelists.

(1) Female Troubled by Hair Color Damages and Curl-Associated Low Styling Ease

The hair cosmetic composition was sprayed onto the shampooed and towel-dried hair. After the hair cosmetic composition was spread with a brush, the hair was brush-and-blow finished with a dryer. When the hair cosmetic composition had been used for 5 days as described above, advantageous effects were observed such that the hair was styled tidy, curled-up hair ends and flyaways were eliminated, the hair was provided with sleekness, and the hair gave a smooth touch feel without stiffness.

(2) Female Having Her Hair Wave-Permed About 1 Month Ago

The hair cosmetic composition was sprayed onto the shampooed and towel-dried hair. After the hair cosmetic composition was spread with a brush, the hair was dried with a dryer. When the hair cosmetic composition had been used for 5 days as described above, advantageous effects were observed such that the hair was provided with attractive permanent waves and sleekness and the hair gave a smooth touch feel without stiffness.

(3) Female Troubled by the Lack of Body and Volume in Her Hair Due to Aging and a Hair Color The hair cosmetic composition was sprayed onto the shampooed and towel-dried hair. After the hair cosmetic composition was spread with a brush, the hair was dried with a dryer. When the hair cosmetic composition had been used for 5 days as described above, advantageous effects were observed such that the hair was provided with body and vitality, was volumized to fluff out, and was provided with sleekness.

Example 5

Pump Spray

|  | (wt %) |
|---|---|
| Malic acid | 2.50 |
| Lactic acid | 2.50 |
| Stearyl trimethylammonium chloride | 0.25 |
| Glycerol | 1.00 |
| 2-Benzyloxyethanol | 2.50 |
| Ethanol | 4.50 |
| Fragrance | 0.02 |
| Water | Balance |
| Sodium hydroxide (pH adjuster) | Sufficient to Adjust to pH 3.7 |

Example 6

Pump Mist

|  | (wt %) |
|---|---|
| Malic acid | 4.00 |
| Lactic acid | 1.00 |
| 2-Benzyloxyethanol | 2.50 |
| Polyvinylpyrrolidone | 3.00 |
| Ethanol | 10.00 |
| Fragrance | 0.05 |
| Water | Balance |
| Sodium hydroxide (pH adjuster) | Sufficient to Adjust to pH 3.7 |

Example 7

Hair Gel

|  | (wt %) |
|---|---|
| Malic acid | 2.50 |
| Lactic acid | 2.50 |
| Glycerol | 2.00 |
| Stearyl trimethylammonium chloride | 0.25 |
| 2-Benzyloxyethanol | 2.50 |
| Hydroxyethylcellulose | 2.00 |
| Ethanol | 10.00 |
| Fragrance | 0.05 |
| Water | Balance |
| Sodium hydroxide (pH adjuster) | Sufficient to Adjust to pH 3.7 |

Example 8

Hair Lotion

|  | (wt %) |
|---|---|
| Malic acid | 1.00 |
| Lactic acid | 4.00 |
| Stearyl trimethylammonium chloride | 0.25 |
| Glycerol | 1.00 |
| 2-Benzyloxyethanol | 2.50 |
| Ethanol | 10.00 |
| Fragrance | 0.02 |
| Water | Balance |
| Sodium hydroxide (pH adjuster) | Sufficient to Adjust to pH 3.7 |

Example 9

Aerosol Spray

|  | (wt %) |
|---|---|
| <Concentrate> |  |
| Malic acid | 2.50 |
| Lactic acid | 2.50 |
| Stearyl trimethylammonium chloride | 0.25 |
| Glycerol | 1.00 |
| 2-Benzyloxyethanol | 2.50 |
| Ethanol | 4.50 |
| Fragrance | 0.02 |
| Water | Balance |
| Sodium hydroxide (pH adjuster) | Sufficient to Adjust to pH 3.7 |
| <Propellant> |  |
| Nitrogen gas |  |
| <Concentrate/propellant ratio> | 99.50/0.50 |

Example 10

Pump Foam

|  | (wt %) |
|---|---|
| Malic acid | 2.50 |
| Lactic acid | 2.50 |
| Polyoxyethylene lauryl ether (16 E.O.) | 1.00 |
| Stearyl trimethylammonium chloride | 0.25 |
| Glycerol | 1.00 |
| 2-Benzyloxyethanol | 2.50 |
| Ethanol | 4.50 |
| Fragrance | 0.02 |
| Water | Balance |
| Sodium hydroxide (pH adjuster) | Sufficient to Adjust to pH 3.7 |

Example 11

Aerosol Foam

|  | (wt %) |
|---|---|
| <Concentrate> |  |
| Malic acid | 4.00 |
| Lactic acid | 1.00 |
| Polyoxyethylene lauryl ether (16 E.O.) | 1.00 |
| Stearyl trimethylammonium chloride | 0.25 |
| Glycerol | 1.00 |
| 2-Benzyloxyethanol | 2.50 |
| Ethanol | 4.50 |
| Fragrance | 0.02 |
| Water | Balance |
| Sodium hydroxide (pH adjuster) | Sufficient to Adjust to pH 3.7 |
| <Propellant> |  |
| LPG (0.44 Mpa) |  |
| <Concentrate/propellant ratio> | 93.00/7.00 |

Example 12

Hair Lotion

|  | (wt %) |
|---|---|
| Malic acid | 2.5 |
| Lactic acid | 2.5 |
| 2-Benzyloxyethanol | 2.5 |
| Stearyl trimethylammonium chloride | 0.25 |
| Polyethylene glycol 400 | 0.45 |
| Ethanol | 4.5 |
| Water | Balance |
| Sodium hydroxide (pH adjuster) | Sufficient to Adjust to pH 3.7 |

The invention claimed is:

1. A method for modifying hair property, which comprises applying a hair cosmetic composition comprising:
    (a) 0.1 to 10 wt. % of malic acid or a salt thereof;
    (b) 0.01 to 10 wt. % of lactic acid or a salt thereof;
    (c) 0.1 to 10 wt. % of an organic solvent selected from the group consisting of benzyl alcohol and benzyloxyethanol;
    (d) 1 to 50 wt. % of ethanol; and
    (e) a hair setting polymer
    to said hair, and then warming said hair
    wherein a ratio of ethanol to component (c) is from 40:1 to 2:1
    wherein a pH, at 25° C. of a solution diluted 20-fold in water is from 2.5 to 4.5 and
    wherein said composition is left on said hair.

2. The method for modifying hair property of claim 1, wherein component (a) is present in an amount of 0.5 to 10 wt. %.

3. The method for modifying hair property of claim 1, wherein component (b) is present in an amount of 0.5 to 10 wt. %.

4. The method according to claim 1, wherein a weight ratio of (a) malic acid or a salt thereof to (b) lactic acid or a salt thereof is from 10/1 to 1/10 weight ratio being determined based on a weight of free acid.

5. The method according to claim 1, further comprising an oil ingredient.

6. The method for modifying hair property of claim 5, wherein said oil ingredient is a silicone present in an amount of 0.05 to 20 wt. %.

7. The method for modifying hair property of claim 1, further comprising 0.01 to 10 wt. % of a surfactant.

8. The method for modifying hair property of claim 1, further comprising 0.1 to 10 wt. % a polyhydric alcohol.

9. The method for modifying hair property of claim 1, wherein component (c) is present in an amount of 0.5 to 5 wt. %.

10. The method for modifying hair property of claim 1, wherein component (d) is present in an amount of 1 to 20 wt. %.

11. The method for modifying hair property of claim 1, wherein said hair setting polymer is at least one polymer selected from the group consisting of
    a polyvinylpyrrolidone-based high molecular compound;
    an acidic vinyl-ether based, high molecular compound;
    an acidic polyvinyl-acetate based, high molecular compound;
    an acidic acrylic high molecular compound;
    an amphoteric acrylic high molecular compound;

a basic acrylic high molecular compound;
a cationic cellulose derivative; and
hydroxypropyl chitosan, carboxymethyl chitin and carboxymethyl chitosan.

12. The method for modifying hair property of claim 1, wherein said hair setting polymer is at least one polymer selected from the group consisting of
a polyvinylpyrrolidone-based high molecular compound;
an acidic vinyl-ether based, high molecular compound;
an acidic polyvinyl-acetate based, high molecular compound;
an acidic acrylic high molecular compound;
an amphoteric acrylic high molecular compound; and
a basic acrylic high molecular compound.

13. The method for modifying hair property of claim 1, wherein said hair setting polymer is a polyvinylpyrrolidone-based molecular weight compound.

14. The method for modifying hair property of claim 13, wherein said polyvinylpyrrolidone-based molecular weight compound is at least one compound selected from the group consisting of polyvinylpyrrolidone, vinylpyrrolidone/vinyl acetate copolymer, vinylpyrrolidone/vinyl acetate/vinyl propionate terpolymer, vinylpyrrolidone/alkyl aminoacrylate (quaternized) copolymers, vinylpyrrolidone/acrylate/(meth)acrylic acid copolymers, vinylpyrrolidone/alkyl aminoacrylate/vinylcaprolactam copolymers.

15. The method for modifying hair property of claim 1, wherein said hair setting polymer is an amphoteric acrylic high molecular weight compound.

16. The method for modifying hair property of claim 15, wherein said amphoteric acrylic high molecular weight compound is at least one compound selected from the group consisting of N-methacryloylethyl-N,N-dimethylammonium-alpha-N-methylcarboxybetaine/butyl methacrylate copolymer and hydroxypropyl acrylate/butylaminoethyl methacrylate/octylacrylamide copolymer.

17. The method for modifying hair property of claim 1, wherein said hair setting polymer is an acidic vinyl-ether based high molecular weight compound.

18. The method for modifying hair property of claim 17, wherein said acidic vinyl-ether based high molecular weight compound is a methyl vinyl ether/ alkyl half ester of maleic anhydride copolymer.

19. The method for modifying hair property of claim 1 wherein said hair setting polymer is a basic acrylic high molecular compound.

20. The method for modifying hair property of claim 19, wherein said basic acrylic high molecular weight compound is an acrylamide-acrylate quadripolymer.

21. The method for modifying hair property of claim 1, wherein said hair setting polymer is present in an amount of 0.1 to 10 wt. %.

22. The method for modifying hair property of claim 1, wherein said hair setting polymer is present in an amount of 0.5 to 5 wt. %.

23. The method for modifying hair property of claim 6, wherein said silicone is at least one silicone selected from the group consisting of dimethylpolysiloxane, polyether-modified silicones, amino-modified silicones, carboxyl-modified silicones, methylphenylpolysiloxane, fatty-acid-modified silicones, alcohol-modified silicones, aliphatic-alcohol-modified silicones, epoxy-modified silicones, fluorine-modified silicones, cyclic silicones, and alkyl-modified silicones.

24. The method for modifying hair property of claim 7, wherein said surfactant is a cationic surfactant.

25. The method for modifying hair property of claim 24, wherein said cationic surfactant is at least one cationic surfactant selected from the group consisting of cetyl trimethylammonium chloride, stearyl trimethylammonium chloride, arachyl trimethylammonium chloride and behenyl trimethylammonium chloride.

* * * * *